United States Patent [19]

Talmage et al.

[11] Patent Number: 4,675,160
[45] Date of Patent: Jun. 23, 1987

[54] OCCULT BLOOD TEST MONITOR

[75] Inventors: Joseph M. Talmage, Landing; Norman H. Oksman, Mountain Lakes, both of N.J.

[73] Assignee: Warner-Lambert Company, Morris Plains, N.J.

[21] Appl. No.: 823,215

[22] Filed: Jan. 28, 1986

[51] Int. Cl.⁴ .................... G01N 21/78; G01N 33/72
[52] U.S. Cl. ........................................ 422/56; 422/57; 436/66; 436/904
[58] Field of Search .................. 422/56-58, 422/61; 436/66, 904

[56] References Cited

U.S. PATENT DOCUMENTS

| 2,838,377 | 6/1958 | Fonner | 436/66 |
| 3,323,710 | 2/1966 | Reickmann et al. | 416/205 |
| 3,996,006 | 12/1976 | Pagano | 422/55 |
| 4,175,923 | 11/1979 | Friend | 422/56 |
| 4,365,970 | 12/1982 | Lawrence et al. | 436/66 |
| 4,486,536 | 12/1984 | Baker et al. | 422/58 X |
| 4,541,987 | 9/1985 | Guadagno | 422/56 |

FOREIGN PATENT DOCUMENTS

| 0085261 | 8/1983 | European Pat. Off. . |
| 0093595 | 11/1983 | European Pat. Off. . |
| 0124214 | 11/1984 | European Pat. Off. . |
| 0124215 | 11/1984 | European Pat. Off. . |
| 1018563 | 1/1966 | United Kingdom | 436/66 |

Primary Examiner—Barry S. Richman
Assistant Examiner—Robert J. Hill, Jr.
Attorney, Agent, or Firm—Howard Olevsky; Gary M. Nath

[57] ABSTRACT

An in-the-bowl occult blood test is provided with a flushable matrix having a separate testing site which will indicate the presence of residual oxidizing compounds in the toilet.

8 Claims, 1 Drawing Figure

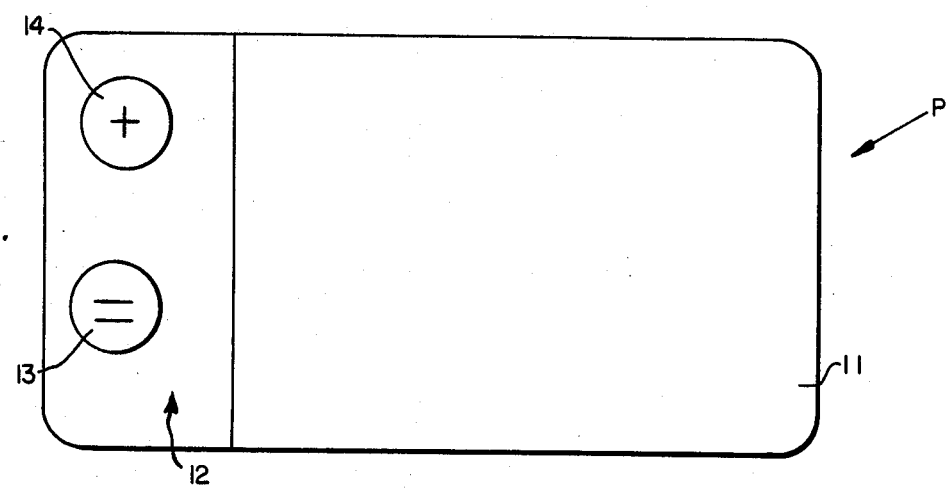

OCCULT BLOOD TEST MONITOR

BACKGROUND OF THE INVENTION

This invention relates to a testing monitor useful for detection of peroxidase-like activity and, in particular, a test kit for detection of such activity in stool samples containing a testing monitor.

The detection of peroxidase-like activity was found to be indicative of the presence of hemoglobin in a specimen and, reported to be correlated to the heightened fertility period in females during the estrous cycle. The detection of peroxidase-like activity has, therefore, become an invaluable aid to the medical practitioner.

Over 100,000 persons in the United States are affected by cancer of the colon and rectum each year. When the number of colorectal cancers occurring each year is combined with the number of cancers occurring in other digestive organs, including the esophagus and stomach, such cancers of the digestive system account for more occurrences of cancer than any other single form of the disease.

Contrary to many other forms of cancer, early diagnosis and treatment of digestive tract cancer results in the cure rate of 80 to 90% of those affected. This cure rate drastically decreases as cancer reaches its later stages. Thus, early detection of the disease is critical to successful treatment.

Most, but not all cancers of the digestive tract bleed to a certain extent. Blood found in the gastric contents and in vomitus is indicative to conditions associated with disorders of the mucous membrane, such as ulcers, diverticulitis, colitis and carcinoma. In addition, blood is also deposited in fecal matter extruded frm the digestive system. The presence of blood in fecal matter is not normally detected, however, until gross bleeding occurs. When this is evident, digestive tract cancers are in their advanced stages.

Various test equipment and procedures have been developed for use by physicians in testing for the presence of occult blood in fecal matter. One of the most successful tests is manufactured and held by Smith Kline Diagnostics of Sunnyvale, Calif. under the trademark "Hemoccult." The package for the Hemoccult test is disclosed in U.S. Pat. No. 3,996,006 issued to J. Pagano. Briefly, the Pagano test employs an absorbent white paper impregnated with a guaiac reagent and encased in a special test slide having openable flaps on both sides. To use the Pagano test slide, one must obtain a sample for fecal matter, smear it onto the guaiac-impregnated paper by opening the panel on one side of the test slide, and then close the panel. A panel on the opposite side of the test slide is then opened and contacted with a developing agent. The developing agent is a stabilized solution of hydrogen peroxide and denatured alcohol which is applied to the guaiac-impregnated paper. If occult blood is present in the fecal matter smeared on the opposite side of the paper, the product of the guaiac reaction will appear as a blue substance against the white paper background, providing a positive indication of the presence of blood in the fecal matter. The Pagano test is designed for evaluation by a diagnostic laboratory. As a test which can be evaluated at home, the Pagano test has two short comings. First, it requires the person to handle fecal matter and secondly, it requires the tester to be somewhat sophisticated when interpretating the results.

There is another problem inherent in the Pagano test and other tests which require laboratory interpretation. This problem relates to the difference in time between the taking of the sample and its evaluation. Of course, there is the obvious problem of storing the test kit after the sample has been taken and, since it is desirable to minimize the premature decomposition of the reactants, the sample must be kept cold. Refrigerator storage of fecal samples is obviously unpopular when the refrigerator storage space must be shared by food utilized by the consumer.

A more serious problem with clinical tests is disclosed in "Gastroenterology 1982"; 1982-986-91 in which it is stated that prolonged storage in desiccation can affect the reliability of the guaiac-impregnated slide test in detecting fecal occult blood. The reliability of the test is related to hemoglobin concentration; a slightly positive reaction can become negative upon storage and a test yielding strong positivity for blood can convert to less pronounced or even ambiguous results. The exact reason for this apparent time dependent conversion is not known, although it is assumed that the denaturation of hemoglobin in stool by proteolytic enzymes and bacteria occurs. It has been shown by this reference that a concentration of hemoglobin and stool may produce a very strong positive reaction which is stable for thirty days whereas a weak positive response will become negative on the sixth day after specimen application. For these reasons, it is apparent that a test which can be conducted reliably by the individual in this own home and which can yield readily discernably results is the test method of choice.

A non-clinical test is disclosed by D. E. Fonner in U.S. Pat. No. 2,838,377. The Fonner test utilizes O-tolidine and benzidine. The reagents when mixed with blood and other reactants produce a visible dye. The Fonner test employs a testing apparatus which can be dropped into the toilet bowl. The Fonner test has, however, not been particularly successfully because of the high rate of false positive indications associated with it.

The ideal test, therefore, should be one which can be conducted as an in-house test with monitors to eliminate false positive or false negative readings. Also the test should be designed to eliminate the manual handling of stool samples or stool sample-contaminated testing matrixes.

U.S. Pat. No. 4,175,923 issued to William G. Friend discloses a test which utilizes a test strip which is dropped in the toilet bowl. A portion of the test strip contains blood which will react with the other components of the test coating, e.g., guaiac and peroxide to produce the blue color which is characteristic of a positive test for occult blood and, therefore, provides the user with a ready frame of reference for the color change associated with a positive test.

U.S. Pat. No. 3,323,710 issued to P. Rieckmann et al. discloses the use of a strip having a sealed preprinted color indicator comparison test area for ready comparison when a color indicator test is performed.

U.S. Pat. No. 4,365,970 issued to Paul J. Lawrence et al. describes a occult blood test with apparatus similar to that disclosed in Pagano and Friend having, in addition, built in positive and negative performance monitors in the form of two small spots. One of these spots contains a blood component. The other spot is guaiac treated paper. When the developer solution is applied to the spot containing the blood component its color change indicates that the developer solution is efficacious. If there is a color change present from the addition of the developer solution to the negative control, there is a defect in the test paper which destroys the efficacy of the test.

U.S. Pat. No. 4,541,987 issued to P. A. Guadagno discloses an in-bowl toilet test with a so-called positive control site employing the test reagent, a peroxygen compound and a small amount of catalyst that would always yield positive results. If no color change occurred in this control area when the area was wet, the test would be shown to be defective. A second control is also disclosed which is an area containing only the peroxygen composition. According to this patent, a color change at this area would indicate a contaminant in the pad, or improper manufacture. This analysis is only true if the paper inherently has a substitute for both haem and oxygen sensitive dye. While this is disclosed as a test for toilet bowl contamination, it would not produce a color change with residual strong oxidants only.

U.S. patent application No. 491,008 entitled "Specimen Collection Wipe for Occult Blood Detection" filed May 3, 1983 assigned to the assignee of the invention and subject to a notice of allowance also discloses the concept of an indicator activity verification region which changes color to monitor the efficacy of the testing reagent. A neutral response region is also provided to eliminate the possibility of false positives due to contamination of the paper.

While the prior art test comparison verification procedures are beneficial toward increasing the efficacy of the readings of the results of these tests, none of these tests monitor the presence of pre-existing contaminants in the toilet bowl water. Strong oxidizing agents are routinely used to clean toilet bowls and tend to contain compounds such as hypochlorites for their function as a bleaching agent. These and other strong oxidizing agents may provide oxidative residues which produce a false positive test.

SUMMARY OF THE INVENTION

According to this invention a flushable monitor is formed which changes color when contacted by residual oxidizing compounds present in the toilet bowl. Also contemplated is a testing matrix utilizing this invention.

DETAILED DESCRIPTION OF THE INVENTION

The instant inventive concept, like those of the prior art, is based upon the detection of peroxidase-like activity present in hemoglobin and biological fluids. This perioxidase-like activity, also referred to as catalytically active subtances in the case of blood are identified in hemoglobin. These substances belong to the general class of hemoproteins, conjugate proteins all of which have the same prosthetic group, i.e., iron protoporphyrin or haem. This prosthetic group has the ability to catalyze the transfer of oxygen from an oxygen source to an acceptor which in turn becomes oxidized. The acceptor is a colorless precursor until it becomes oxidized, wherein the oxidized form indicates the presence of the peroxidase-like activity by color formation.

Conventional toilet bowl cleansers are strong oxidizing agents, e.g., hypochlorites or other oxidizing bleaches. Traces of these agents may be present in the toilet bowl after the toilet has been cleaned. Trace amounts may adhere to the bowl especially in areas where there is minimal water contact such as under the rim. These amounts may gradually leach out into the toilet water over a period of time and provide a replacement for the peroxidase-like reaction associated with occult blood presence. Residual toilet bowl contamination is also a problem with certain of the in-bowl cleansers which contain strong oxidizing agents and are delivered in measured aliquots along with fresh toilet water after each flush. In the presence of these oxidizing agents, tests designed to detect occult blood through the mechanism of pseudoperoxidase activity will yield a false positive color change.

The test monitor of this invention is a flushable guaiac or other oxygen sensitive dye-impregnated paper which changes color in response to the presence of this residual oxidizing agent. This monitor may be used by merely dropping it in the toilet bowl prior to or after defecation either prior to or along with an in-home, occult blood detection test.

Contrary to Guadagno, this monitor reacts to a contaminant which is likely to be found in a toilet bowl, i.e., strong oxidizing agents, rather than an unlikely contaminant combination which must contain its own oxygen sensitive dye to change color.

If the monitor is to be used as part of a test matrix after defecation, it is preferably floatable to be easier reading. In any event, the monitor will only change color because of residual oxidizing agent, because no other source of oxidizing agent is available to it.

The test matrix employing the monitor of this invntion is flushable, porous, cellulosic sheet and contains a plurality of sites impregnated with different combinations of reagents as will be explained in more detail below.

There are three distinct reactive types of sites useful in the particularly preferred embodiment of the subject invention. The first is associated with sample testing and contains an oxygen sensitive dye and a peroxygen source which is designed to liberate active oxygen by the presence of peroxidase-like substances in the occult blood sample, thereby producing the appropriate color change.

A second site is a positive activity indicator characterized by the presence of an oxygen sensitive dye, a peroxygen source and a reagent containing a haem-based component which will produce a color reaction upon being wet regardless of the presence of an independent source of perioxidase-like activity.

The third type of test site is a toilet contaminant monitor embodying the inventive concept of the invention and this site contains only guaiac or other suitable oxygen sensitive dye. When this site contacts the fluid in the toilet bowl it will only turn color in the presence of a residual strong oxidizing agent. This is true because with only the oxygen sensitive dye present the only means for providing the color change would be the residual oxidizing agent in the toilet bowl.

Any of the oyxgen sensitive dye components customarily used in these types of indicator reactions are suitable according to the concept of this invention and they include for example, gum guaiac and its derivatives, aniline and its derivitive, o-tolidine, o-toluidine, p-toluidine, benzidine, tetramethylbenzidene, di-anisidine, o-cresol, m-cresol, alpha naphthol beta naphthol, catechol, guaiacol, pyrogallol and mixtures thereof. The preferred indicator material is guaiac because of its recognition as an effective indicator, its non-carcinogenicity and commercial availability. In the presence of an oxygen source and peroxidase-like activity, gum guaiac changes from colorless to a blue color.

The detection of peroxidase activity has become an invaluable aid to the medical practitioner for the diagnosis of a number of disorders. One of the most widely used indicator reagents for diagnosing occult-blood is derived from an extract from the wood of certain species of trees of the Guaiacum genus native to the American tropics. The extract, termed guaiac, turns from essentially colorless to blue in the presence of hemoglobin and a peroxygen source such as hydrogen peroxide. More specifically, the guaiac reagent when accompanied by a peroxygen source is sensitive to what is termed "peroxidase activity" which is present in hemoglobin or certain chemically similar compounds.

The preparation of solution formulations of the oxygen sensitive dye for deposition in the test matrix is governed by the absorbability of the particular matrix employed and upon the desired sensitivity i.e., the extent of the color change desired for a particular level of pseudo-peroxygen activity. Preferred amounts of oxygen sensitive dye may range from 0.01% to about 3.0% and preferably about 0.25% to about 2.0% by weight based upon the weight of the entire formulation. Amounts above about 3% are not desired since they may result in hypersensitivity showing false positive results. Amounts below about 0.01% are not recommended since they do not provide sufficient color development for accurate detection of peroxidase-like activity.

A buffer is added to the oxygen sensitive dye formulations in solution as part of the paper coating to aid in stability and to provide the optimum pH value to enable catalytic activity to occur. It is essential that the buffer selected maintain the pH within a range in which the indicator material changes color upon oxidation. Normally this will be between a pH of about 2 and about 8 and preferably between about 3 and about 5. Higher pH values should be avoided to prevent autooxidation of the indicator, resulting in false positive results. Lower pH values inhibit efficient oxidation. Representative buffers include citrate, tartrate, phosphate, acetate and mixtures thereof with citrate buffers being preferred.

The peroxygen source is dissolved or suspended in an organic solvent for deposition on the matrix. A wide range of organic solvents may be used which are nonreactive with the formulation ingredients. Representative organic solvents include compounds selected from
(1) ethers, such as diethyl ether, diisopropyl ether;
(2) ketones, such as acetone, methylethylketone, methylisobutylketone;
(3) aromatic hydrocarbons such as benzene and toluene;
(4) chlorinated hydrocarbons such as methylene chloride, chloroform, carbon tetrachloride;
(5) acids, such as acidic and propionic and mixtures thereof. Most preferred solvents are selected from the group consisting of chlorinated solvents, aromatic hydrocarbons and mixtures thereof.

The peroxygen source is selected from materials that will yield hydrogen peroxide in the presence of water. Hemoglobin or other peroxidase activator is the catalytic agent that promotes the reaction between the indicator and the peroxygen source to produce the indicator color change.

Representative peroxygen source materials include both organic and inorganic peroxides. Illustrative compounds include monopersulfates, cumene hydroperoxide, butyl hydroperoxidemonopersulfates and mixtures thereof.

A preferred peroxygen source is a monopersulfate salt which is adhered to the matrix with polyvinylpyrrolidone. A particularly preferred perioxide is sold by Dupont Company under the trademark "Oxone" which comprises two moles of potassium monopersulfate, one mole of potassium hydrogensulfate and one mole of potassium sulfate. The Oxone TM suspension is prepared by suspending 25 to 250 milligrams per milliliter of a suitable organic solvent such as chloroform.

The composition useful for coating the indicator portion of the invention may be prepared by routine procedures. The examples set forth below is designed to be illustrative only. Alternative oxygen sensitive dyes and peroxide containing compositions are well known and readily adaptable to the subject invention.

BRIEF DESCRIPTION OF THE DRAWING

FIG. 1 is a plan view of an embodiment of the testing matrix of this invention.

DETAILED DESCRIPTION OF THE DRAWING

Referring now to FIG. 1 a particularly preferred embodiment of the invention is depicted in which the test paper P having a sample testing site 11 treated with an oxygen sensitive dye such as guaiac and a peroxygen source such as "Oxone TM" is positioned separately from a portion containing two separate test sites. Site 14 contains the oxygen sensitive dye, a peroxygen source and a haem component as will be discussed in more detail below. The haem component provides a source of peroxidase-like activity such that all of the reactants are present in the dry state to produce the color reaction indicative of a positive test. Also at test area 12 there is a test site 13 which has only a guaiac solution impregnated on it.

When the testing matrix shown in FIG. 1 is put into a toilet bowl, the act of wetting the area of site 14 will produce a blue color change if all of the reactants in the system are efficacious. If occult blood is present, the sample test area 11 will make the appropriate color change, such as a blue color in the case of a guaiac oxygen sensitive dye.

Test site 13, however, will only change color in the presence of a source of a strong oxidizing agent contaminant in the toilet bowl. Since there is no peroxide present at the test site the only available oxygen possible for the oxygen sensitive dye must be found from the available separately in the toilet bowl. Thus, if the color chage occurs at site 13 as well as the sample test site 11 it is unknown whether occult blood is present and another test should be taken to indicate whether the positive result is false. If sites 11 and 14 change color the test is efficacious and occult blood is likely to be present. Of course, there is no circumstance except for the failure of the peroxygen to react which would produce a color change at the test site 13 but not at the collection site 11.

A method of this invention is illustrated in the discussion associated with the example as indicated below.

EXAMPLE

Sheets of Whatman No. 1 filter paper and a solution were prepared for impregnating test sample collection sites 11, 13 and 14 in the following manner.

| Ingredient | Preferred Amount | Range |
| --- | --- | --- |
| Gum Guaiac Solution | | |
| Gum guaiac | 3.5 mg/ml | 2-20 mg/ml |
| Citric acid | 3.0 mg/ml | 0.5-10 mg/ml |
| Ethanol | 75% v/v | 50-90% v/v |
| Water | 25% v/v | 10-50% v/v |
| Oxone Suspension | | |
| Oxone | 100 mg/ml | 25-250 mg/ml |
| PVP | 20 mg/ml | 10-100 mg/ml |
| Chloroform | q.s. | q.s. |
| Hematin Solution | | |
| Hematin | 0.06 mg/ml | 0.03-0.12 mg/ml |
| IN NaOH | 2.5 mg/ml | 1.2-5.0 mg/ml |
| Ethanol | 50% v/v | 35-65% v/v |
| Water | 50% v/v | 35-65% v/v |

Referring to FIG. I, the gum guaiac solution is deposited at sites 11, 13 and 14 and dried by heating at elevated temperatures not exceeding 60° C. for several minutes. Then the hematin solution was deposited at test site 14. Finally, the "Oxone ™" suspension is deposited at sites 11 and 14 and dried. The test devices are packated in an air-tight, moisture barrier pouch for long term stability.

Three separate test indicator matrices were prepared as described above. The first was added to tap water and in that instance only site 14 containing the haem component in addition to the guaiac and peroxygen source showed a blue color change. A second matrix was added to a second container containing an aqueous solution of blood and in that instance sites 11 and 14 changed color. In the third container containing dilute hypochlorite solution indicative of a common bowl cleaner, the third matrix showed a reaction at all test sites. The fact that site 13 changed color is indicative of strong oxidizing agent contamination present in the bowl. The color change at site 13 indicates that the color change at site 11 is not necessarily due to the presence of occult blood.

If this occurs the user of the test should take appropriate action to eliminate strong oxidizing agent contamination and rerun the test until subsequent tests show no color change of the monitor at site 13.

The invention being thus described, it will be obvious that the same may be varied in many ways. Such variations are not to be regarded as a departure from the spirit and scope of the invention and all such modifications are intended to be included within the scope of the following claims.

We claim:

1. An in-bowl testing matrix in the form of a flushable, porous, cellulosic sheet, for determining the presence of occult blood in a stool sample comprising in combination;
    (a) means for testing a stool sample which includes a substrate containing thereon an oxygen sensitive dye and a peroxygen source capable of reacting with each other in the presence of occult blood to produce an indication of the presence of occult blood; and
    (b) a toilet contaminant monitor testing means consisting essentially of a substrate having thereon an oxygen sensitive dye reactable with strong oxidizing agents present as contaminants in a solution to produce an indication of the presence of such strong oxidizing agents.

2. The matrix of claim 1 further containing a contaminant monitor means cooperatively associated therewith for testing the efficacy of the oxygen sensitive dye and peroxygen source present on the stool sample testing means.

3. The matrix of claim 1 wherein the oxygen sensitive dye of (a) and/or (b) is selected from the group consisting of guaiac, guaiac derivatives, aniline, aniline derivatives, o-tolidine, o-toluidine, p-toluidine, benzidine, tetramethylbenzidine, di-anisidine, o-cresol, m-cresol, alphanaphthol, catechol, guaicol, pyrogallol and mixtures thereof.

4. The matrix of claim 1 wherein the oxygen sensitive dye of (a) and/or (b) is gum guaiac.

5. The matrix of claim 4 wherein gum guaiac is buffered to a pH of 2 and 6 prior to its application to the matrix.

6. The matrix of claim 1 wherein the peroxygen source is selected from the group consisting of compositions which yield hydrogen peroxide in the presence of water.

7. The matrix of claim 6 wherein the peroxygen source is a monopersulfate salt.

8. The matrix of claim 7 wherein the monopersulfate salt is adhered to the substrate of the stool sample testing means with polyvinylpyrrolidone.

* * * * *